United States Patent [19]

Mosbach

[11] 4,335,094

[45] Jun. 15, 1982

[54] MAGNETIC POLYMER PARTICLES

[76] Inventor: Klaus H. Mosbach, Lackalänga 31-38, S-240 20 Furulund, Sweden

[21] Appl. No.: 21,603

[22] PCT Filed: Jun. 1, 1978

[86] PCT No.: PCT/SE78/00001

§ 371 Date: Feb. 2, 1979

§ 102(e) Date: Jan. 26, 1979

[87] PCT Pub. No.: WO78/00005

PCT Pub. Date: Dec. 7, 1978

[51] Int. Cl.$^3$ ............................................. G01N 33/56
[52] U.S. Cl. ..................................... 424/1; 23/230 B; 424/9; 424/12; 424/1.5
[58] Field of Search .......................... 424/1, 12, 9, 1.5; 23/230 B

[56] References Cited

U.S. PATENT DOCUMENTS

| | | |
|---|---|---|
| 3,970,518 | 7/1976 | Giaever .................................. 424/12 |
| 3,985,649 | 10/1976 | Eddelman ........................... 210/42 S |
| 4,106,488 | 8/1978 | Gordon .................................... 424/1 |
| 4,115,534 | 12/1978 | Ithakissios .............................. 424/1 |
| 4,172,253 | 12/1979 | Davies et al. ........................... 424/1 |

OTHER PUBLICATIONS

Nye et al., Clinica Chimica Acta, vol. 69, No. 2, Jun. 1976, pp. 387-396.
Ithakissios et al., Clinica Chimica Acta, vol. 84, No. 1/2, Mar. 1978, pp. 69-84.

*Primary Examiner*—Christine M. Nucker
*Attorney, Agent, or Firm*—Beveridge, DeGrandi & Kline

[57] ABSTRACT

This invention relates to magnetic polymer particles as carriers of biologically, preferably pharmaceutically, active substances, the utilization of the magnetic polymer particles, the method of retaining a biologically active substance, preferably a pharmaceutically active substance within a restricted area, and the method of treating diseased tissue with the use of the magnetic polymer particles.

39 Claims, No Drawings

MAGNETIC POLYMER PARTICLES

This invention relates to magnetic polyer particles and the process for their production and utilization.

More particularly, the invention relates to magnetic polymer particles as carriers of biologically, preferably pharmaceutically, active substances, the utilization of the magnetic polymer particles, the method of retaining a biologically active substance, preferably a pharmaceutically active substance within a restricted area, and the method of treating diseased tissue with the use of the magnetic polymer particles.

Magnetic polymer particles as carriers of biologically active substances, preferably pharmaceutically active substances, should be useful within many technical and medicinal fields because they can be concentrated by the application of a magnetic field.

The present invention provides magnetic polymer particles as carriers of biologically, preferably pharmaceutically active substance, said particles being particles of a preferably porous polymer in the pores or lattice of which magnetic material is deposited, and the biologically active substance being associated with the polymer.

Further, the invention comprises a method of producing magnetic polymer particles as carriers of biologically, preferably pharmaceutically active substance, in which method particles of a preferably porous polymer, which may carry the biologically active substance, and/or polymerizable monomers are contacted with a colloidal solution of a magnetic material and, optionally, non-associated biologically active substance, the optionally present monomers are polymerized, the solvent is optionally removed, the magnetic material and the optionally present, non-associated biologically active substance being deposited in the pores or lattice of the polymer particles, and the resulting magnetic polymer particles are then associated with the pharmaceutically active substance unless said substance is already associated with the polymer particles.

The invention also comprises the utilization of the magnetic polymer particles as carriers of biologically, preferably pharmaceutically active substance, the substance being associated with particles of a preferably porous polymer and magnetical properties being imparted to said particles by treatment with a magnetic material in the form of particles or colloidal solution.

The invention in addition provides a method of retaining a biologically, preferably pharmaceutically active substance within a restricted area, in which method the substance is associated with a carrier in the form of preferably porous polymer particles to which magnetic properties are imparted by treatment with a magnetic material in the form of particles or a colloidal solution, and the magnetic carrier with the substance associated therewith is then retained within the restricted area by application of a magnetic field.

Finally, the invention provides a method of treating a diseased tissue, in which an effective amount of a pharmaceutically active substance is concentrated in said tissue by the substance being supplied to the tissue associated with a carrier in the form of magnetic, preferably porous polymer particles and concentrated to the diseased tissue by application of a magnetic field.

As polymer use can be made for instance of a polysaccharide, preferably agarose or starch. Another suitable polymer is acrylic polymer. The polymer should be biocompatible. A particular advantage, when used in the treatment of mammals, is gained if the polymer is biodegradable, such as starch which is enzymatically degraded in the organism. Polymers forming too small lattices are unsuitable.

The magnetic material is used in the form of particles of a colloidal solution, preferably colloidal ferrite. Colloidal ferrite is commercially available as ultramicroscopical (about 100 A) ferrite particles surrounded by a thin layer (about 25 A) of a polymer. The particles are prevented by said polymer layer from adhering to each other in a magnetic field. Random collisions (Brownian motion) with the molecules of the carrier liquid retain the particles in colloidal solution. As has been mentioned, particulate magnetic material can also be incorporated with the polymer particles according to the invention. A suitable material is particulate ferrite, $Fe_3O_4$ or nickel.

According to the present invention the magnetic polymer particles which contain colloidal magnetic material are produced in a very advantageous manner by contacting already formed, preferably porous polymer which may have associated biological ligands, with a colloidal solution of magnetic material. After optional removal of the solvent of the magnetic material, said magnetic material remains in the polymer, probably by precipitation in the pores or lattice of the polymer, whereby the polymer obtains magnetic properties. In this manner, polymer particles already produced can be made magnetical afterwards. Polymers which are already substituted with biological ligands are commercially available, which makes this method extremely advantageous. If the polymer which has thus been made magnetic does not already have associated ligands, said polymer is then contacted with a biologically active substance which is thereby associated with the polymer serving as a carrier of the substance.

In another embodiment of the production process according to the invention, magnetic polymer particles are produced by polymerization of say acrylic monomers in presence of a colloidal solution of magnetic material, said magnetic material remaining in the resulting polymeric lattice. Another way is to contact say acrylic monomers simultaneously with the colloidal solution of magnetic material and agarose, the acrylic monomers being polymerized. To the magnetic polymer particles thus formed, biological ligands can be associated for instance by the so-called BrCN-method.

In a further embodiment of the production process according to the invention the polymer particles are produced by polymerization of a monomer in the simultaneous presence of a crosslinking agent, the colloidal solution of magnetic material and the pharmaceutically active substance. In this process both the magnetic material and the pharmaceutically active substance are locked up in the polymeric lattice. To thereby work with a colloidal solution of the magnetic material instead of particulate magnetic material is very convenient. This process can be performed for instance by polymerization of alkyl monomers in the presence of cross-linking agent, enzyme (such as trypsin) and Ferrofluid (colloidal solution of ferrite particles, trademark).

Magnetic polymer particles can also be produced in that a particulate magnetic material is contacted with polymerizable monomers or a solution of a polysaccharide, such as agarose or starch, in which case the magnetic polymers will be incorporated with the lattice of the polymer. These magnetic polymer particles are then contacted with the biologically active substance, whereby said biologically active substance will be associated with the magnetic polymer particles.

The magnetic polymeric particles according to the invention, which contain colloidal magnetic material, can be used for instance at so-called affinity chromatography, for instance to separate enzymes from a mixture of several different enzymes. To this end, for instance an enzyme inhibitor which may be either a specific inhibitor or a general inhibitor or cofactor, is associated with the magnetic polymer particles. By specific inhibitor is meant an inhibitor specific to but one enzyme, and this is the case with most inhibitors, whereas a general inhibitor can inhibit several different enzymes. When these polymer particles with inhibitors associated therewith are added to a solution of several different enzymes, the inhibitors will bind the enzymes, and after agitation for some time it is possible to separate the contemplated enzyme or enzymes by applying a magnetic field within or without the solution. The magnetic particles will collect at the magnet and the remainder of the solution can be removed. The enzymes can then be separated from the inhibitors bound to the magnetic carrier by methods well-known to those skilled in the art. As an example of this use there may be mentioned postmagnetized Sepharose (available from Pharmacia, Sweden) to which the general inhibitor adenosine monophosphate (AMP) has been adsorbed. Moreover, other enzyme systems, such as glucose-6-phosphate dehydrogenase which has been adsorbed to postmagnetized 2′, 5′-ADP-Sepharose (from Pharmacia, Sweden), have been successfully employed.

The magnetic polymer particles according to the invention can further be used in immuno adsorbance. Antibodies against human serum albumin are thereby associated with Sepharose (from Pharmacia, Sweden) and are postmagnetized by treatment with a colloidal solution of magnetic material. With the aid of the antibodies thus supported on a magnetic carrier human serum albumin can be collected.

As mentioned in the foregoing, the magnetic material can be used either in the form of particles or a colloidal solution according to what is suitable in various uses. Particular advantages are, however, gained with the use of a colloidal solution, int. al. because—as has also been mentioned in the foregoing—polymers already formed can be postmagnetized.

The present invention also provides a very advantageous method of retaining a biologically, preferably pharmaceutically active substance within a restricted area, it being necessary to utilize a much smaller amount of the active substance than would have been the case with the same substance without application of the method of the invention.

As an example of this use there may be mentioned the treatment of thrombi. Proteolytic enzymes, such as plasmine, are known by their ability to dissolve different substrates, among them fibrin (thrombi). By associating these proteolytic enzymes with or enclosing them in the magnetic polymer particles according to the present invention the enzymes can be enriched and retained in position in vivo with the aid of an outer or an inner magnetic field. This will provide a local concentration of the active substance in the treatment of thrombi, whereby the dosis of the proteolytic enzyme can be considerably reduced in relation to the dosis utilized in hitherto known methods.

In a manner analogous to that applied in the treatment of thrombi a general local medicinal treatment can be realized, the active substance, for instance a cytostaticum, being either coupled via a reversable weak bond to the carrier and being then released on the spot where it shall become active, or be fixedly coupled to the carrier, being active in a bound state. In this way a high concentration of the active substance is obtained at the desired spot simultaneously as injurious effects of the active substance in other parts of the organism are avoided.

A further medicinal use in the so-called slow-release of deposits of active substance. Great advantages can be gained by supply of for instance insulin or steroids bound to or enclosed in magnetic polymer particles according to the invention, as deposits, the active substances being retained in the organism by the application of a magnetic field and being permitted slowly to diffuse out.

A further field in which the magnetic particles according to the present invention can be employed is in general chemical, particularly organo-chemical reactions in which the substances to be reacted are first associated with a magnetic carrier according to the present invention, whereupon a very intimate contact is realized between the substances associated with the carrier by the application of a magnetic field. This will produce a high specific reaction without any secondary reactions, that is, very high efficiency, and it is possible to work at low concentrations. Further, an interaction between two or more components can be forced by the application of a magnetic field.

In another very promising embodiment of the present invention live microbes have been successfully baked into gels of polymeric materials such as polysaccharides, together with a colloidal ferrite solution (Ferrofluid). Magnetic immobilized microbes are thereby obtained.

By treating red corpuscles with a colloidal ferrite solution there are obtained highly biocompatible carriers of biological substance. The desired substances can then be associated with these carriers. The initially kidney-shaped corpuscles will become round. Liposomes can also be treated with the colloidal ferrite solution, said solution penetrating into the onion skin-shaped layers of fatty acids and water in the liposomes.

A process for production of magnetic polymer particles according to the invention is illustrated by the following example which should not be considered restrictive to the invention. As will be realized by one of ordinary skill in the art, numerous changes and modifications can be realized without departing from the inventive idea, such as it is defined by the present description and the appended claims.

EXAMPLE

One gram of moist 5′-AMP-(or 2′, 5′-ADP)-Sepharose-4B (Pharmacia) which was previously swollen in 0,1 M sodium phosphate buffer pH 7.5, and washed with $H_2O$ was packed in a column. Subsequently 6.5 ml of ferrofluid (base, $H_2O$; magnetic saturation, 200 G; trademark AO5, from Ferrofluidics Corporation, Burlington, Mass., USA) were pumped through the column and cycled for 4 h at a flow rate of 50 ml $h^{1-}$ (usually at room temperature). After washing with 1 l of $H_2O$, on glass filter, incubation overnight at 4° C. with 100 mg of bovine serum albumin in 0,1 M Tris-HCl buffer pH 7.6, 5 mM in EDTA and 1 mM 2-mercaptoethanol was carried out, followed by washing with 200 ml 1 M NaCl and 200 ml of the same buffer. The dark brown gel beads were then magnetic and ready for use.

Whether the ferrite particles simply adsorb to the gel or precipitate out in the interior of the beads remains to be established. (In this context it should be noted that entrapment of ferrofluid within the lattice of polyacrylamide can easily be accomplished.) In any case, the magnetic properties of the gel remain unchanged after extensive washing with buffer (even washing with, for example, ethanol or 40% ethylene glycol did not remove the ferrite particles) and repeated use in magnetic fields; they are strong enough to allow rapid sedimentation even when applying weak permanent magnets.

I claim:

1. Magnetic polymer particles as carriers of biologically active substance comprising
   particles of a polymer having a lattice or pores;
   a biologically active substance associated with said polymer particles, and
   magnetic material deposited in said lattice or pores wherein said magnetic material is deposited by contacting the polymer particles with a colloidal solution comprising said magnetic material.

2. Magnetic polymer particles as carriers of biologically active substance, comprising
   particles of a polymer, which is derived from polymerizable monomers, said particles having a lattice or pores,
   a biologically active substance associated with said polymer particles, and
   magnetic material deposited in said lattice or pores, wherein said magnetic material is deposited by contacting the polymerizable monomers with a colloidal solution comprising said magnetic material.

3. Magnetic polymer particles as claimed in claim 1 or 2, wherein the biologically active substance is pharmaceutically active.

4. Magnetic polymer particles as claimed in claim 1 or 2, wherein the biologically active substance is selected from the group consisting of an enzyme inhibitor, an enzyme, a cytostaticum, a radio nucleotid, insulin, a steroid and a live microbe.

5. Magnetic polymer particles as claimed in claim 1 or 2 wherein the biologically active substance is a proteolytic enzyme.

6. Magnetic polymer particles as claimed in claim 1 or 2, wherein the polymer is porous.

7. Magnetic polymer particles as claimed in claim 1 or 2, wherein the polymer is biodegradable.

8. Magnetic polymer particles as claimed in claim 1 or 2, wherein the polymer is selected from the group consisting of an acrylic polymer, and a polysaccharide.

9. Magnetic polymer particles as claimed in claim 1 or 2, wherein the polymer is selected from the group consisting of agarose and starch.

10. Magnetic polymer particles as claimed in either of claims 1 or 2, wherein the magnetic material is colloidal.

11. Magnetic polymer particles as claimed in claim 9, wherein the magnetic material is colloidal ferrite.

12. A process for the production of magnetic polymer particles as carriers for biologically active substance comprising the step of contacting polymer particles having a lattice or pores, which particles carry the biologically active substance, with a colloidal solution of magnetic material, such that the magnetic material is deposited in the pores or lattice of said polymer particles.

13. A process for the production of magnetic polymer particles as carriers for biologically active substance comprising the step of contacting polymer particles having a lattice or pores with a colloidal solution of magnetic material and the biologically active substance, such that the magnetic material and the biologically active substance are deposited in the pores or lattice of said polymer particles.

14. A process for the production of magnetic polymer particles as carriers for biologically active substance comprising the steps of contacting polymer particles having a lattice or pores with a colloidal solution of magnetic material such that the magnetic material is deposited in the pores or lattice of said polymer particle, and associating the biologically active substance with the magnetic polymer particles.

15. A process for the production of magnetic polymer particles as carriers for biologically active substance comprising the steps of contacting polymerizable monomers in a colloidal solution of magnetic material and polymerizing said monomers, such that said magnetic material is deposited in pores or a lattice of the resulting polymer particles, and associating the biologically active substance with the magnetic polymer particles.

16. A process for the production of magnetic polymer particles as carriers for biologically active substance comprising the steps of contacting polymerizable monomers in a colloidal solution of magnetic material and the biologically active substance and polymerizing said monomers, such that said magnetic material and the biologically active substance are deposited in pores or a lattice of the resulting polymer particles.

17. The process according to claim 12, 13 or 14 wherein said colloidal solution contains a solvent and said process further comprises the step of removing solvent from said colloidal solution of magnetic material after said contacting step.

18. The process according to claim 15 or 16 wherein said colloidal solution contains a solvent and said process further comprises the step of removing solvent from said colloidal solution of magnetic material after said polymerization step.

19. A process as claimed in any one of claims 12 to 16, wherein there is associated with the magnetic polymer particles as biologically active substance a pharmaceutically active substance.

20. A process as claimed in any one of claims 12 to 16, wherein there is associated with the magnetic polymer particles as biologically active substance a substance selected from the group consisting of an enzyme inhibitor, an enzyme, a cytostaticum, a radio nucleotid, insulin, a steroid and a live microbe.

21. A process as claimed in any one of claims 12 to 16, wherein there is associated with the magnetic polymer particles as biologically active substance a proteolytic enzyme.

22. A process as claimed in any one of claims 12 to 16, wherein as polymer particles use is made of porous polymer particles.

23. A process as claimed in any one of claims 12 to 16, wherein use is made of a biodegradable polymer.

24. A process as claimed in any one of claims 12 to 16, wherein as polymer particles use is made of particles selected from the group consisting of an acrylic polymer and a polysaccharide.

25. A process as claimed in any one of claims 12 to 16, wherein as polymer particles use is made of particles selected from the group consisting of agarose and starch.

26. A process as claimed in claim 15 or 16, wherein an acrylic monomer is inserted as polymerizable monomer.

27. A process as claimed in any one of claims 12 to 16, wherein colloidal ferrite is used as magnetic material.

28. A method of retaining a biologically active substance within a restricted area, characterized in that the biologically active substance is associated with particles of a polymer, which particles are given magnetic properties by incorporation of a magnetic material in the form of a colloidal solution, whereupon a magnetic field is applied to the restricted area for retaining the magnetic polymer particles with the substance associated therewith.

29. A method of retaining a biologically active substance as described in claim 28, wherein the substance is pharmaceutically active.

30. A method of retaining a biologically active substance as described in claim 28, wherein the polymer is porous.

31. A method of retaining a biologically active substance as described in claim 28, wherein the polymer is biodegradable.

32. A method of retaining a biologically active substance as described in claim 28, wherein the polymer is selected from the group consisting of red corpuscles, particles of a liposome, an acrylic polymer and a polysaccharide.

33. A method of retaining a biologically active substance as described in claim 32, wherein said polymer is agarose or starch.

34. A method of treating a diseased tissue, characterized in that an effective amount of a pharmaceutically active substance is concentrated in the tissue by supply of the substance to the tissue associated with a carrier in the form of polymer particles, which have been given magnetic properties by incorporation of a magnetic material in the form of a colloidal solution, and that the magnetic carrier with the associated pharmaceutical substance is concentrated to the diseased tissue by the application of a magnetic field.

35. A method of treating a diseased tissue as described in claim 34, wherein the polymer is porous and/or biodegradable.

36. Magnetic starch particles as carriers of biologically active substance comprising
particles of starch having a lattice or pores;
a biologically active substance associated with said starch particles, and
magnetic material deposited in said lattice or pores wherein said magnetic material is deposited by contacting starch particles with a colloidal solution comprising saig magnetic material.

37. A method of retaining a biologically active substance within a restricted area, characterized in that the biologically active substance is associated with particles of starch, which particles are given magnetic properties by incorporation of a magnetic material in the form of a colloidal solution, whereupon a magnetic field is applied to the restricted area for retaining the magnetic starch particles with the substance associated therewith.

38. A method of treating a diseased tissue, characterized in that an effective amount of a pharmaceutically active substance is concentrated in the tissue by supply of the substance to the tissue associated with a carrier in the form of starch particles, which have been given magnetic properties by incorporation of a magnetic material in the form of a colloidal solution, and that the magnetic carrier with the associated pharmaceutical substance is concentrated to the diseased tissue by the application of a magnetic field.

39. A process for the production of magnetic starch particles as carriers for biologically active substance comprising the step of contacting starch particles having a lattice or pores, which particles carry the biologically active substance, with a colloidal solution of magnetic material, such that the magnetic material is deposited in the pores or lattice of said starch particles.

* * * * *